(12) United States Patent
Hung

(10) Patent No.: US 6,365,693 B1
(45) Date of Patent: Apr. 2, 2002

(54) FLUOROALKANESULFONYL AZIDE COPOLYMERS

(75) Inventor: Ming-Hong Hung, Wilmington, DE (US)

(73) Assignee: DuPont Dow Elastomers, L.L.C., Wilmington, DE (US)

( * ) Notice: Subject to any disclaimer, the term of this patent is extended or adjusted under 35 U.S.C. 154(b) by 0 days.

(21) Appl. No.: 09/553,165

(22) Filed: Apr. 19, 2000

Related U.S. Application Data

(60) Provisional application No. 60/133,066, filed on May 7, 1999.

(51) Int. Cl.$^7$ .............................................. C08F 228/02
(52) U.S. Cl. ...................................... 526/288; 526/247
(58) Field of Search ................................ 526/288, 242, 526/247, 250

(56) References Cited

U.S. PATENT DOCUMENTS

| | | | |
|---|---|---|---|
| 3,282,875 A | 11/1966 | Connolly et al. | |
| 3,718,627 A | 2/1973 | Grot | |
| 3,997,571 A | 12/1976 | Buckley et al. | |
| 4,281,092 A | 7/1981 | Breazeale | 526/247 |
| 4,564,717 A | 1/1986 | Ohmori et al. | 568/843 |
| 4,640,885 A | 2/1987 | Lenox et al. | 430/197 |
| 5,059,720 A | 10/1991 | Hung | 568/674 |
| 5,399,758 A | * 3/1995 | Miura et al. | 564/150 |

FOREIGN PATENT DOCUMENTS

| | | | |
|---|---|---|---|
| EP | 0 829 471 A2 | 3/1998 | C07C/261/02 |
| WO | WO 99/10423 | 3/1999 | C08K/5/43 |

OTHER PUBLICATIONS

Shi–Zheng Zhu, Synthesis and Reactions of Fluoroalkanesulfonyl Azides and N,N–Dichlorofluoroalkanesulfonamides, *J. Chem. Soc. Perkin Trans.*, 2077–2081, 1994.

Shi–Zheng Zhu, Synthesis of Fluoroalkanesulfonyl Azides and Their Reactions as Fluroalkanesulfonyl Nitrene Precursors, *Tetrahedron Letter*, 33, 6503–4, 1992.

* cited by examiner

*Primary Examiner*—Christopher Henderson

(57) ABSTRACT

Fluorinated olefins and fluorinated vinyl ethers, each having sulfonyl azide groups, are useful monomers in preparing fluoropolymers having functional side groups. Such functional side groups are useful in curing the fluoropolymers and also for enhancing the adhesion of the fluoropolymers to other substrates.

9 Claims, No Drawings

FLUOROALKANESULFONYL AZIDE COPOLYMERS

CROSS-REFERENCE TO RELATED APPLICATION

This application claims the benefit of U.S. Provisional Application No. 60/133,066 filed May 7, 1999.

FIELD OF THE INVENTION

This invention relates to both fluoroalkanesulfonyl azide compounds which are useful as functional monomers in fluoropolymers and to the fluoropolymers which contain units derived from such fluoroalkanesulfonyl azide monomers.

BACKGROUND OF THE INVENTION

Fluoroelastomers must generally be cured in order to develop the physical properties necessary for most end use applications. Often, the fluoroelastomer must contain a curesite monomer such as $CF_2=CFOCF_2CF(CF_3)OCF_2CF_2-CN$ (U.S. Pat. No. 4,281,091) in order to be cured. Such curesite monomers require long exposure to high temperature and the presence of catalyst(s) to complete the curing. However, catalyst residues may adversely affect the properties of the cured fluoroelastomer article, or byproducts of the curing reaction may pose environmental problems. Long exposure to high temperatures may increase manufacturing costs and can cause polymer degradation Thus, there is a need for curesite monomers which do not require catalysts or long exposure to high temperatures in order to crosslink fluoroelastomers.

There is also a need for fluoropolymers having functional side groups for improving the adhesion of fluoropolymers to other substrates (such as metal surfaces or other polymers), for improved durability of fluoropolymer coatings, and for providing crosslinking to improve the mechanical properties of the fluoropolymers.

SUMMARY OF THE INVENTION

The present invention provides a new class of functional monomers having a sulfonyl azide group. Copolymerizing these monomers with at least one other (i.e. different) fluorinated monomer, and (optionally) a fluorine-free monomer, provides a fluoropolymer having a reactive fluoroalkanesulfonyl azide side group which can form crosslinks in fluoropolymers without the need for catalysts or exposure to high temperatures for long periods of time. The sulfonyl azide side group may also be used to enhance adhesion between the fluoropolymer and another substrate, improve the durability of coatings, and increase the mechanical properties of the fluoropolymer through crosslinking.

Specifically, an embodiment of this invention is a fluoroalkanesulfonyl azide compound of the formula $$CF_2=CF-(O)_p-R_f-(CH_2)_n-S(O)_qN_3 \quad (I)$$

wherein p=0 or 1; n=0–4; q=1 or 2; and $R_f$ is a $C_1$–$C_{16}$ perfluoroalkyl or perfluoroalkoxy group. Preferably, p=1; n=0; q=2 and $R_f$ is selected from the group consisting of $-CF_2CF(CF_3)OCF_2CF_2-$ and $-(CF_2)_m-$, wherein m=2–4.

A second embodiment of this invention is a fluoroalkanesulfonyl azide compound of the formula $$CX_1X_2=CX-(O)_p-R_f-(CH_2)_n-S(O)_qN_3 \quad (II)$$

wherein X, $X_1$, $X_2$ are independently H or F (with the proviso that X, $X_1$, and $X_2$ can not all be F, so that compound II is not identical to compound I); p=0 or 1; n=0–4; q=1 or 2; and $R_f$ is a perfluoroalkyl or perfluoroalkoxy group. Preferably, X, $X_1$, $X_2$ are H; p=0; n=0; q=2; and $R_f$ is $-CF_2CF_2OCF_2CF_2-$ or $-(CF_2)_y-$, wherein y=1–8.

A third embodiment of this invention is a copolymer comprising units derived from compound (I) or compound (II) and units derived from at least one other fluorinated monomer.

DETAILED DESCRIPTION OF THE INVENTION

It has been discovered that certain fluoroalkylsulfonyl azide compounds are useful as monomers in making fluoropolymers, and are particularly useful in minor amount to introduce highly reactive functional side groups into the fluoropolymer. Such fluoropolymers are useful materials in the areas of curable elastomers and elastoplastics, adhesion enhancement, coatings, thermosetting resins, grafting polymers and the like. Under the appropriate thermal or photo initiation conditions, the sulfonyl azide functional group is able to generate a highly reactive nitrene species. The nitrene intermediate may then undergo either a coupling or an insertion reaction, thereby crosslinking the fluoropolymer chains.

A first embodiment of this invention is a fluoroalkanesulfonyl azide compound of the formula $$CF_2=CF-(O)_p-R_f-(CH_2)_n-S(O)_qN_3 \quad (I)$$

wherein p=0 or 1; n=0–4; q=1 or 2; and $R_f$ is a $C_1$–$C_{16}$ perfluoroalkyl or perfluoroalkoxy group. Preferably, p=1; n=0; q=2 and $R_f$ is selected from the group consisting of $-CF_2CF(CF_3)OCF_2CF_2-$ and $-(CF_2)_m-$, wherein m=2–4. Specifically, these species include, but are not limited to, $CF_2=CFOCF_2CF(CF_3)OCF_2CF_2-SO_2N_3$ (8-SAVE); $CF_2=CFOCF_2CF_2-SO_2N_3$; $CF_2=CFOCF_2CF_2CF_2-SO_2N_3$; and $CF_2=CFOCF_2CF_2CF_2CF_2-SO_2N_3$.

A second embodiment of this invention is a fluoroalkanesulfonyl azide compound of the formula $$CX_1X_2=CX-(O)_p-R_f-(CH_2)_n-S(O)_qN_3 \quad (II)$$

wherein X, $X_1$, $X_2$ are independently H or F (with the proviso that X, $X_1$ and $X_2$ can not all be F); p=0 or 1; n=0–4; q=1 or 2; and $R_f$ is a perfluoroalkyl or perfluoroalkoxy group. Preferably, X, $X_1$, $X_2$ are H; p=0; n=0; q=2; and $R_f$ is $-CF_2CF_2OCF_2CF_2-$ or $-(CF_2)_y-$, wherein y=1–8. A specific example is $CH_2=CHCF_2CF_2OCF_2CF_2-SO_2N_3$.

When q=1 in formula I or II, the monomers of this invention are more correctly described as "fluoroalkanesulfonyl azides". However, for simplicity, the monomers of this invention are collectively referred to herein as fluoroalkanesulfonyl azides, regardless of whether q=1 or 2.

The general process for making the fluoroalkanesulfonyl azide compounds of this invention is to react sodium azide with the appropriate fluoroalkanesulfonyl fluoride, fluoroalkanesulfonyl bromide, or fluoroalkanesulfonyl chloride at a temperature between −20° to 50° C. (preferably between 0° to 20° C.) in a solvent such as methanol, acetonitrile, acetone, or mixtures thereof.

Copolymers of this invention comprise i) units derived from either compound (I) or compound (II) of this invention and ii) units derived from at least one other fluorinated monomer. By "other fluorinated monomer" is meant a copolymerizable fluoromonomer other than a fluoroalkanesulfonyl azide. In addition, copolymers may contain units derived from one or more fluorine-free monomers.

Preferably, units derived from compound (I) or compound (II) are present in minor amounts in the copolymers of this invention. Typically, copolymers contain 0.02–10 mole percent (based on the total monomer units in the polymer) of units derived from either compound (I) or compound (II), preferably 0.1–5 mole percent and most preferably 0.3–3 mole percent.

Fluorinated monomers suitable for forming copolymers with compound (I) or compound (II) include, but are not limited to: tetrafluoroethylene (TFE); chlorotrifluoroethylene (CTFE); trifluoroethylene; vinylidene fluoride (VF2); vinyl fluoride (VF); hexfluoropropylene (HFP); 1- or 2-hydropentafluoropropylene, 3,3,3-trifluoropropylene; hexafluoroisobutylene; perfluoro(alkyl vinyl ethers) (PAVE) having alkyl groups containing 1–5 carbon atoms (preferably 1–3 carbon atoms); perfluoro(alkoxy vinyl ethers) having alkoxy groups containing 1–5 carbon atoms; perfluoro-(2,2-dimethyl-1,3-dioxole) (PDD) and perfluoro-(2-methylene-4-methyl-1,3-dioxolane) (PMD). Also included in this group of fluorinated monomers are perfluoro (alkyl vinyl ethers) which contain functional groups such as acid fluorides or esters. Examples of these ethers include $CF_2=CFOCF_2CF(CF_3)OCF_2CF_2SO_2F$ (PSEPVE) and $CF_2=CFOCF_2CF(CF_3)OCF_2CF_2COOCH_3$ (EVE). Preferably, at least one of the fluorinated monomers is selected from the group consisting of TFE, CTFE and VF2.

Fluorine free monomers that can be used in the copolymers of this invention include: ethylene, propylene, n-butylene, iso-butylene, vinyl acetate (VAc), and vinyl ethers such as methyl vinyl ether.

The copolymers of this invention may be glassy, thermoplastic or elastomeric. They may be amorphous or partially crystalline, melt-fabricable or non-melt-fabricable. One skilled in the art will readily recognize that such polymer properties are controlled by the type of monomers used in the copolymer and their relative levels.

Typical elastomeric copolymers of this invention comprise, in addition to minor amounts of units derived from either compound (I) or compound (II), units derived from a combination of monomers selected from the group consisting of a) VF2 and HFP; b) VF2, HFP and TFE; c) VF2, PAVE and TFE; d) TFE and PAVE; e) TFE and propylene; f) TFE, VF2 and propylene; and g) TFE, PAVE and ethylene.

Typical thermoplastic copolymers of this invention comprise, in addition to units derived from either compound (I) or compound (II), units derived from either TFE or CTFE and up to 10 mole percent of one or more additional monomers such as HFP, PDD, PMD and ethylene.

Copolymers of this invention may be prepared by any of the known processes for producing fluoropolymers. Such processes may be conducted, for example, in an aqueous or non-aqueous medium, or in mixed media as is well known in the art. As is likewise well known in the art, dispersion, emulsion, solution or suspension processes may be employed, and the processes may be conducted on a continuous, batch or semi-batch basis.

The copolymer emerging from the reactor may be isolated and dried by any known technique, taking care that the polymer is not heated enough to cause crosslinking. Alternatively, an aqueous dispersion emerging from the reactor may be used directly as-is, for example as a coating composition, or it may first be stabilized by addition of surfactant and/or concentrated by processes well known in the art for the preparation of latex coating compositions.

Copolymers of this invention may be cured by exposure to UV radiation or heat. In addition, copolymers of this invention may be mixed with other curable polymers and curing agents and the resulting mixture co-cured. The copolymers of this invention may also be mixed with additives, processing aids and fillers well known in the rubber and plastics industries such as, but not limited to, carbon black, mineral fillers including barium sulfate, talc and silica, fibrillating or non-fibrillating thermoplastic fluoropolymers, metal oxides, metal hydroxides and the like.

EXAMPLES

Melting temperature ($T_m$) and glass transition temperature ($T_g$) were measured by differential scanning calorimetry (DSC). As is conventional, $T_m$ was taken as the peak of the melting endotherm for partially-crystalline polymers, while $T_g$ was taken as the point of slope change in the DSC trace for non-crystalline copolymers.

Monomer compositions were determined by $^1H$ and $^{19}F$ NMR spectroscopy and infrared spectroscopy (IR).

Copolymer compositions were determined by $^{19}F$ NMR at high temperature or in a suitable swelling solvent. Temperature was such that the sample was in the melt state, that is above $T_m$ for partially crystalline samples, and above $T_g$ for non-crystalline samples. IR was used to detect the presence of the azide (~2150 $cm^{-1}$) and sulfonyl (~1430 $cm^{-1}$) groups incorporated into the copolymers.

Example 1

Preparation of perfluoro-[2-(2-azidosulfonylethoxy) propyl vinyl ether] [$CF_2=CFOCF_2CF(CF_3)OCF_2CF_2—SO_2N_3$] (8-SAVE)

Perfluoro-[2-(2-fluorosulfonylethoxy)propyl vinyl ether] (PSEPVE) was synthesized by reaction of tetrafluoroethylene with $SO_3$ to form a sultone, followed by reaction with hexafluoropropylene oxide and pyrolysis as disclosed in Prog. Rubber Plast. Technol., vol. 4, p 258 (1993). A reaction flask was then charged with sodium azide (6.55 g, 0.1 mol) and PSEPVE (44.6 g, 0.10 mol) in a mixed solvent of anhydrous methanol (100 ml) and anhydrous acetonitrile (10 ml). The mixture was stirred at ambient temperature for 48 hours. The solid residue was filtered and discarded. The filtrate was poured into ice-water and the bottom organic layer was collected. The organic layer was washed with water, dried over sodium sulfate and distilled to give a clear, colorless liquid which was identified by IR and $^{19}F$ NMR as 8-SAVE. The 8-SAVE had a boiling point (b.p.) of 61–62° C. at 5 mm Hg. Yield: 20 g (42.6%). Pertinent NMR and IR data follow: $^{19}F$ NMR (376.89 MHz, $CDCl_3$): −78.7 (m, 2F), −80.3 (m, 3F), −85.0 (m, 2F), −113.5 (s, 2F), −113.4, −113.5, −113.6, −113.7 (4s, 1F), −121.5, −121.7, −121.8, −122.0 (4m, 1F), −135.6, −135.8, −135.9, −136.1 (4m, 1F), −144.9 (t, J=21.8 Hz, 1F); IR (neat): 2153 $cm^{-1}$ (—$SO_2N_3$), 1840 $cm^{-1}$ ($CF_2=CFO$), 1425 $cm^{-1}$.

Example 2

Preparation of perfluoro-[2-(2-azidosulfonylethoxy) propyl vinyl ether] [$CF_2=CFOCF_2CF(CF_3)OCF_2CF_2—SO_2N_3$]

A reaction flask was charged with sodium azide (13.1 g, 0.2 mol) and PSEPVE (89.2 g, 0.20 mol) in a mixed solvent of anhydrous methanol (80 ml) and anhydrous acetonitrile (80 ml). The mixture was stirred at ambient temperature for 20 hours and then at 40° C. for 3 hours. The product was isolated as described in Example 1. After distillation, 58 g of the sulfonyl azide was obtained (62% yield).

Example 3

Preparation of perfluoro-[2-(2-azidosulfonylethoxy) propyl vinyl ether] [$CF_2=CFOCF_2CF(CF_3)OCF_2CF_2-SO_2N_3$]

A reaction flask was charged with sodium azide (39 g, 0.60 mol) and PSEPVE (267.6 g, 0.60 mol) in a mixed solvent of anhydrous methanol (250 ml) and anhydrous acetonitrile (200 ml). The mixture was stirred at ambient temperature for 12 hours and then at 40° C. for 6–7 hours. The product was isolated as described in Example 1. After distillation, 129 g of the sulfonyl azide was obtained (46% yield), bp. 52–54° C. at 3 mm Hg.

Example 4

Preparation of perfluoro-[(2-azidosulfonyl)ethyl vinyl ether] [$CF_2=CFOCF_2CF_2-SO_2N_3$]

Sodium azide (22.8 g, 0.35 mol) was suspended in a mixed solvent consisting of anhydrous methanol (125 ml) and anhydrous acetonitrile nitrile (100 ml). Perfluoro-2-(fluorosulfonyl)ethyl vinyl ether (84 g, 0.30 mol) (available from Dow Chemical Co., see also Ezzell et al. U.S. Pat. No. 4,358,412 and Kawaguchi et al. Japanese Patent No. 52-33610) was added slowly via a syringe to the reaction flask while the reaction temperature was controlled at 20°–25° C. After the addition was complete, the reaction mixture was stirred at ambient temperature for approximately 15 hours and then at 35°–40° C. for 3 hours. The reaction mixture was cooled and the product mixture was added to ice water. The lower organic layer was separated, washed several times with water, and dried over sodium sulfate to afford perfluoro-[(2-azidosulfonyl)ethyl vinyl ether] as a clear, colorless liquid, yield 48.1 g (53.3%). $^{19}F$ NMR and IR confirmed the identity of the product: $^{19}F$ NMR (376.89 MHz, CDCl$_3$): −83.3 (s, 2F), −113.4 (s, 2F), −113.1 (m, 1F), −121.2 (m, 1F), −135.8 (m, 1F); IR (neat): 2156 cm$^{-1}$ (−SO$_2$N$_3$), 1840 cm$^{-1}$ (CF$_2$=CFO), 1464 cm$^{-1}$, 1422 cm$^{-1}$. Small amounts of N$_3$CF$_2$—CFHOCF$_2$CF$_2$—SO$_2$F (and/or −SO$_2$N$_3$) were also obtained as byproducts: $^{19}F$ NMR (376.89 MHz, CDCl$_3$): −81.6 to −84.4 (m, 2F), −91.3 (m, 2F), −113.2 (2F), −143.5 (d, J=41.5 Hz, 1F, −CFH).

Example 5

Preparation of 3-oxa-1,1,2,2,4,4,5,5-octafluoro-6-heptene sulfonyl azide: [$CH_2=CH-CF_2CF_2OCF_2CF_2-SO_2N_3$]

A 1300 ml stainless steel shaker tube was charged with 5-iodo-perfluoro-(3-oxa-pentane) sulfonyl fluoride [$ICF_2CF_2OCF_2CF_2-SO_2F$] (213 g, 0.50 mol) [available from the Shanghai Institute of Organic Chemistry, or it may be prepared according to the methods described in G. A. Bargigia, et al., *J. Fluorine Chem.*, 19, 403 (1982) and Shanghai Quangming Electroplating Factor, *Huaxue Xuebao*, 35, 209 (1977)], (R)-(+)-limonene (0.5 g) and ethylene gas (22.4 g, 0.80 mol). The tube was sealed and heated with agitation at 220° C. for 10 hours. The reaction tube was cooled and the product mixture was decanted from the shaker tube. It was washed with saturated aqueous sodium bisulfite solution to remove residual iodine. The mixture was then distilled to give a clear, light pink liquid, bp. 55° C. at 7–8 mm Hg, which was identified as 7-iodo-3-oxa-1,1,2,2,4,4,5,5-octafluoroheptane sulfonyl fluoride [$ICH_2CH_2CF_2CF_2OCF_2CF_2-SO_2F$] by $^{19}F$ NMR, $^1H$ NMR and IR. Yield: 160 g (70.5%). Pertinent spectroscopy data follow: $^1H$ NMR (400 MHz, CDCl$_3$): δ3.22 (t, J=8.2 Hz, 2H), 2.67 (m, 2H); $^{19}F$ NMR (376.89 MHz, CDCl$_3$): −82.6 (m, 2F), −87.7 (m, 2F), −112.6 (m, 2F), −119.1 (t, J=17 Hz, 2F), +45.0 (m, 1F, —SO$_2$F); IR (neat): 1463, 1445 cm$^{-1}$ (−SO$_2$—).

The 7-iodo-3-oxa-1,1,2,2,4,4,5,5-octafluoroheptane sulfonyl fluoride thus prepared (136.2 g, 0.30 mol) was dissolved in 200 ml anhydrous acetonitrile in a reaction flask which was then heated at 75°–80° C. Triethylamine (38 g, 0.38 mol) was added slowly to the solution. The reaction mixture was then stirred for approximately 16 hours at 75°–80° C. Gas chromatography indicated that all the starting material was consumed. The reaction mixture was cooled to 0°–5° C. and neutralized slowly with concentrated sulfuric acid until the pH of the solution was about 1.0. At this time a two-layer mixture was formed. The bottom organic layer was separated and washed with water, dried over magnesium sulfate, and distilled to give a clear, colorless liquid, bp. 115–116.5° C. Yield: 40 g (41%). The liquid was identified by $^1H$ NMR, $^{19}F$ NMR and IR as 3-oxa-1,1,2,2,4,4,5,5-octafluoro-6-heptene sulfonyl fluoride [$CH_2=CHCF_2CF_2OCF_2CF_2-SO_2F$]:

$^1H$ NMR (400 MHz, CDCl$_3$): δ5.80–6.10 (m, 3H); $^{19}F$ NMR (376.89 MHz, CDCl$_3$): −82.6 (m, 2F), −87.9 (t, J=12.5 Hz, 2F), −112.6 (m, 2F), −118.1 (d, J=9.8 Hz, 2F), +45.0 (m, 1F, —SO$_2$F); IR (neat): 1654 cm$^{-1}$ (CH$_2$=CH—), 1464 cm$^{-1}$ (−SO$_2$—).

In a reaction flask, sodium azide (7.0 g, 0.108 mol) was suspended in a mixed solvent consisting of anhydrous methanol (50 ml) and anhydrous acetonitrile (40 ml) at ambient temperature. 3-oxa-1,1,2,2,4,4,5,5-octafluoro-6-heptene sulfonyl fluoride [prepared above] (32.6 g, 0.1 mol) was added slowly and the reaction temperature was maintained at 20°–25° C. After the addition was complete, the reaction mixture was stirred for 16 hours at ambient temperature. The product mixture was then added to ice water and the bottom organic layer was separated. This layer was washed with water, dried over magnesium sulfate and gave a clear, colorless liquid, identified by $^1H$ NMR, $^{19}F$ NMR and IR as 3-oxa-1,1,2,2,4,4,5,5-octafluoro-6-heptene sulfonyl azide. Yield: 23.0 g (66%). Pertinent NMR and IR data follow: $^1H$ NMR (400 MHz, CDCl$_3$): δ6.01 (m, 2H), 5.80 (m, 1H); $^{19}F$ NMR (376.89 MHz, CDCl$_3$): −81.6 (m, 2F), −88.0 (m, 2F), −113.8 (s, br, 2F), −118.0 (m, 2F); IR (neat): 2288, 2154 cm$^{-1}$ (−SO$_2$N$_3$), 1654 cm$^{-1}$ (CH$_2$=CH—), 1422 cm$^{-1}$ (−SO$_2$—).

Example 6

Polymerization of $CF_2=CFOCF_2CF(CF_3)OCF_2CF_2-SO_2N_3$ (8-SAVE) with tetrafluoroethylene (TFE) and perfluoro-(methyl vinyl ether) (PMVE)

A 400 ml stainless steel shaker tube was charged with de-ionized water (280 ml), ammonium perfluorooctanoate surfactant (1.5 g), disodium phosphate (0.5 g), 8-SAVE [prepared according to the method of Example 1] (4 g), and ammonium persulfate (0.2 g). The tube was sealed and cool-evacuated (i.e. the tube was placed in a dry ice/acetone for several minutes and then evacuated). Perfluoro(methyl vinyl ether) (PMVE) (36 g, 0.217 mol) and tetrafluoroethylene (TFE) (45 g, 0.45 mol) were then introduced into the tube. The tube was sealed and heated to 70° C. for 6 hours. The tube was then cooled and the polymer latex produced during the reaction was coagulated with aqueous magnesium sulfate solution. The polymer thus formed was collected by filtration, and then washed thoroughly with warm water. The polymer was dried in a vacuum oven (150 mm Hg) at 80° C. for 48 hours. A white polymer (58.0 g) was obtained which exhibited a $T_g$ of 0.95° C. Incorporation of 8-SAVE monomer was confirmed by the IR (KBr) absorption at 1431 cm$^{-1}$ and 2149 cm$^{-1}$. The composition of this polymer was determined by high temperature (260° C.) $^{19}$F NMR to be TFE/PMVE/8-SAVE=73.73:25.75:0.52 (mole %).

Example 7

Polymerization of $CF_2=CFOCF_2CF(CF_3)$ $OCF_2CF_2—SO_2N_3$ (8-SAVE) with tetrafluoroethylene (TFE) and perfluoro(methyl vinyl ether) (PMVE)

A 400 ml stainless steel shaker tube was charged with de-ionized water (280 ml), ammonium perfluorooctanoate surfactant (1.5 g), disodium phosphate (0.5 g), 8-SAVE (6.5 g), and ammonium persulfate (0.2 g). The tube was sealed and cool-evacuated. Perfluoro(methyl vinyl ether) (PMVE) (38 g, 0.229 mol) and TFE (45 g, 0.45 mol) were then introduced into the tube. The tube was then sealed and heated at 70° C. for 6 hours. After cooling, the resulting polymer was isolated as described in Example 6. After drying, a white polymer (65.0 g) was obtained which had a $T_g$ of 0° C. No melting point was observed. Incorporation of 8-SAVE monomer was confirmed by the IR (KBr) absorption at 1432 cm$^{-1}$ and 2151 cm$^{-1}$. The composition of this polymer was determined by high temperature (300° C.) $^{19}$F NMR to be TFE/PMVE/8-SAVE=72.31:27.09:0.60 (mole %).

Example 8

Polymerization of $CF_2=CFOCF_2CF(CF_3)$ $OCF_2CF_2—SO_2N_3$ (8-SAVE) with tetrafluoroethylene (TFE)

A 400 ml stainless steel shaker tube was charged with de-ionized water (280 ml), ammonium perfluorononanoate surfactant (2.5 g), disodium phosphate (2.0 g), 8-SAVE (4.0 g), and ammonium persulfate (0.5 g). The tube was sealed and cool-evacuated. TFE (45 g, 0.45 mol) was then introduced into the tube. The tube was then sealed and heated at 70° C. for 4 hours. After cooling, the resulting polymer was isolated as described in Example 6. After drying in a vacuum oven (150 mm Hg) at 75° C. for 48 hours, a white powdered polymer (39.3 g) was obtained which exhibited a broad $T_m$ at 326° C. (2nd heat curve). The incorporation of 8-SAVE monomer was confirmed by the IR (KBr) absorption at 1431 cm$^{-1}$ and 2153 cm$^{-1}$. The composition of this polymer was determined by high temperature (320° C.) $^{19}$F NMR to be TFE/8-SAVE=99.46:0.54 (mole %).

Example 9

Polymerization of $CF_2=CFOCF_2CF(CF_3)$ $OCF_2CF_2—SO_2N_3$ (8-SAVE) with vinylidene fluoride (VF2) and hexafluoropropylene (HFP)

A 400 ml stainless steel shaker tube was charged with de-ionized water (280 ml), ammonium perfluorooctanoate surfactant (1.5 g), disodium phosphate (0.5 g), 8-SAVE (6 g), and ammonium persulfate (0.1 g). The tube was then sealed and cool-evacuated. Vinylidene fluoride ($VF_2$) (54 g, 0.83 mol) and hexafluoropropylene (HFP, 33.6 g, 0.224 mol) were then introduced into the tube. The tube was sealed and heated at 80° C. for 7 hours. After cooling, the resulting polymer latex was coagulated with aqueous magnesium sulfate solution. The polymer formed was collected by filtration, then washed thoroughly with warm water. After drying in a vacuum oven (150 mm Hg) at 80° C. for 15 hours, a white polymer (29.2 g) was obtained which exhibited a $T_g$ of $-20°$ C. Incorporation of 8-SAVE monomer was confirmed by the IR (KBr) absorption at 2157 cm$^{-1}$. The composition of this polymer was determined to be $VF_2$/HFP/ 8-SAVE=92.58/6.90/0.52 (mole %) by $^{19}$F NMR spectroscopy in N,N-dimethylacetamide at 130° C.

Example 10

Polymerization of $CF_2=CFOCF_2CF(CF_3)$ $OCF_2CF_2—SO_2N_3$ (8-SAVE) with perfluoro-(2,2-dimethyl-1,3-dioxole) (PDD) and tetrafluoroethylene (TFE)

A 400 ml stainless steel shaker tube was charged with 1,1,2-trichloro-1,2,2-trifluoroethane (F-113, 150 g), PDD (33 g, 0.135 mol)), 8-SAVE (2 g), and 4,4'-bis(t-butylcyclohexyl)peroxy dicarbonate (0.03 g). The tube was then sealed and cool-evacuated. Tetrafluoroethylene (TFE) (4 g, 0.04 mol) was then introduced into the tube which was then sealed and heated at 70° C. for 6 hours. After cooling, the resulting polymer solution was dried in a 150 mm Hg vacuum oven at 80° C. to remove any residual F-113 solvent. A white tough polymer (28.0 g) was obtained which exhibited a $T_g$ of 196.6° C. Incorporation of 8-SAVE was confirmed by the IR (KBr) absorption at 1431 cm$^{-1}$ and 2149 cm$^{-1}$. The composition of this polymer was determined to be PDD/TFE/8-SAVE=84.65/14.92/0.43 (mole %) by $^{19}$F NMR spectroscopy in hexafluorobenzene at 80° C.

Example 11

Polymerization of $CF_2=CFOCF_2CF(CF_3)$ $OCF_2CF_2—SO_2N_3$ (8-SAVE) with tetrafluoroethylene (TFE), and ethylene (E)

A 400 ml stainless steel shaker tube was charged with 1,1,2-trichloro-1,2,2-trifluoroethane (F-113, 220 ml), cyclohexane (14 ml), perfluorobutylethylene (PFBE, 2 ml), 8-SAVE (8 g), and 4,4'-bis(t-butylcyclohexyl)peroxy dicarbonate (0.1 g). The tube was then sealed and cool-evacuated. Tetrafluoroethylene (TFE), (50 g, 0.50 mol) and ethylene (14 g, 0.50 mol) were then introduced into the tube which was then sealed and heated at 50° C. for 8 hours. After cooling, the resulting polymer solution was dried in a 150 mm Hg vacuum oven at 80° C. for 48 hours to remove any residual F-113 solvent. A white tough polymer (36 g) was obtained which exhibited a $T_m$ at 239.3° C. Incorporation of 8-SAVE was confirmed by the IR (KBr) absorption at 2155 cm$^{-1}$. The incorporation of 8-SAVE in the polymer was determined to be 3.50 mole % (based on the moles of TFE) by $^{19}$F NMR spectroscopy in the melt state at 270° C.

Example 12

Polymerization of $CF_2=CFOCF_2CF(CF_3)$ $OCF_2CF_2—SO_2N_3$ (8-SAVE) with tetrafluoroethylene (TFE), perfluoro-(methyl vinyl ether) (PMVE), and ethylene (E)

A 400 ml stainless steel shaker tube was charged with 1,1,2-trichloro-1,2,2-trifluoroethane (F-113, 200 g), 8-SAVE (4 g), and 4,4'-bis(t-butylcyclohexyl)peroxy dicarbonate (0.1 g). The tube was then sealed and cool-evacuated. Tetrafluoroethylene (TFE) (25 g, 0.25 mol), perfluoro-(methyl vinyl ether) (PMVE) (36 g, 0.217 mol), and ethylene (4 g, 0.143 mol) were then introduced into the tube. The tube was sealed and heated at 70° C. for 7 hours. After cooling, the resulting polymer solution was dried in a 150 mm Hg vacuum oven at 80° C. for 48 hours to remove any residual F-113 solvent. A white tough polymer (27 g) was obtained which exhibited a $T_g$ of $-0.95°$ C. Incorporation of 8-SAVE was confirmed by the IR (KBr) absorption at 1453 cm$^{-1}$ and 2155 cm$^{-1}$. The composition of this polymer was determined to be TFE/PMVE/E/8-SAVE=68.48/13.36/17.43/0.74 (mole %) by $^{19}$F NMR spectroscopy in hexafluorobenzene at 80° C.

What is claimed is:

1. A copolymer comprising:
   a) units derived from a fluoroalkanesulfonyl azide compound selected from the group consisting of those of the formula i) $CF_2=CF-(O)_p-R_f-(CH_2)_n-S(O)_q N_3$ wherein p=0 or 1; n=0–4; q=1 or 2; and $R_f$ is a $C_1-C_{16}$ perfluoroalkyl or perfluoroalkoxy group, and those of formula ii) $CX_1X_2=CX-(O)_p-R_f-(CH_2)_n-S(O)_q N_3$ wherein X, $X_1$, $X_2$ are independently H or F, with the proviso that X, $X_1$, and $X_2$ can not all be F; p=0 or 1; n=0–4; q=1 or 2; and $R_f$ is a perfluoroalkyl or perfluoroalkoxy group; and
   b) units derived from at least one other fluorinated monomer.

2. A copolymer of claim 1 wherein the fluoroalkanesulfonyl azide is

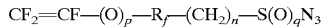

wherein p=0 or 1; n=0–4; q=1 or 2; and $R_f$ is a $C_1-C_{16}$ perfluoroalkyl or perfluoroalkoxy group.

3. A copolymer of claim 2 wherein the fluoroalkanesulfonyl azide is

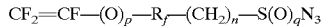

and wherein p=1; n=0; q=2 and $R_f$ is selected from the group consisting of $-CF_2CF(CF_3)OCF_2CF_2-$ and $-(CF_2)_m-$, wherein m=2–4.

4. A copolymer of claim 3 wherein the fluoroalkanesulfonyl azide is $CF_2=CFOCF_2CF(CF_3)OCF_2CF_2-SO_2N_3$.

5. A copolymer of claim 1 wherein the fluoroalkanesulfonyl azide is of the formula

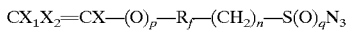

wherein X, $X_1$, $X_2$ are independently H or F; p=0 or 1; n=0–4; q=1 or 2; and $R_f$ is a perfluoroalkyl or perfluoroalkoxy group.

6. A copolymer of claim 5 wherein the fluoroalkanesulfonyl azide is $CH_2=CHCF_2CF_2OCF_2CF_2SO_2N_3$.

7. A copolymer of any one of claims 1 to 6 wherein said other fluorinated monomer is selected from the group consisting of tetrafluoroethylene, chlorotrifluoroethylene and vinylidene fluoride.

8. A copolymer of claim 7 further comprising units derived from at least one fluorinated monomer selected from the group consisting of trifluoroethylene; vinyl fluoride; hexfluoropropylene; 1-hydropentafluoropropylene; 3,3,3-trifluoropropylene; hexafluoroisobutylene; 2-hydropentafluoropropylene; a perfluoro(alkyl vinyl ether) having alkyl groups containing 1–5 carbon atoms, a perfluoro(alkoxy vinyl ether) having alkoxy groups containing 1–5 carbon atoms, perfluoro-(2,2-dimethyl-1,3-dioxole); perfluoro-(2-methylene-4-methyl-1,3-dioxolane) and a perfluoro(alkyl vinyl ether) containing a functional group.

9. A copolymer of claim 7 wherein said other fluorinated monomer is tetrafluoroethylene and further comprising units derived from a fluorine-free monomer selected from the group consisting of ethylene, propylene, n-butylene, isobutylene, vinyl acetate and a vinyl ether.

* * * * *